United States Patent [19]

Ericson

[11] Patent Number: 4,727,565
[45] Date of Patent: Feb. 23, 1988

[54] METHOD OF LOCALIZATION

[76] Inventor: Björn E. Ericson, Grabergsvägen 37, S-310 44 Harplinge, Sweden

[21] Appl. No.: 670,787

[22] Filed: Nov. 13, 1984

[30] Foreign Application Priority Data

Nov. 14, 1983 [SE] Sweden ................ 8306243

[51] Int. Cl.$^4$ .................................... H05G 5/30
[52] U.S. Cl. .................................... 378/205; 378/37; 378/41; 378/163
[58] Field of Search .................. 378/41, 37, 205, 163

[56] References Cited

U.S. PATENT DOCUMENTS

| | | | |
|---|---|---|---|
| 3,577,160 | 5/1971 | White | 378/162 |
| 3,711,712 | 1/1973 | McLaren | 378/163 |
| 4,007,732 | 2/1977 | Kvavle et al. | 378/37 |
| 4,099,880 | 7/1978 | Kano | 378/41 |

FOREIGN PATENT DOCUMENTS 2501436  7/1976  Fed. Rep. of Germany ........ 378/37

OTHER PUBLICATIONS

Björn Nordenström, Hakan Rydèn, and Gunilla Svane, Chapter 5: "Breast" In: Jesus Zornoza, ed., *Percutaneous Needle Biopsy* (Williams & Wilkins, 1981), pp. 43–51.
Rauf Yagan, Ernest Wiesen, Errol M. Bellon, "Mammographic Needle Localization of Lesions Seen in Only One View", *AJR*, vol. 144 (May 1985), pp. 911–916.
Rauf Yagan, Ernest J. Wiesen, Errol M. Bellon, "Breast Lesion Localization in a Single Position" presented in part at the National Conference on Breast Cancer, Honolulu, Hawaii, USA (Mar. 1984), 12 pages.

Primary Examiner—Janice A. Howell
Assistant Examiner—Constantine Hannaher
Attorney, Agent, or Firm—Beveridge, DeGrandi & Weilacher

[57] ABSTRACT

The disclosure relates to a method for localizing the three-dimensional position of a spot in an object in conjunction with X-ray exposure of the object, in which the object is fixed in a pre-determined position and is exposed by means of an exposure apparatus in two directions each on either side of a center line at a right angle to the plane of the image for obtaining a first print and a second print, the two-dimensional position of the target spot on the two prints being established in relation to an index on the prints, and the coordinates of the spot in relation to the indices being processed to obtain control signals for adjustment of a guidance instrument with means for placing in the target spot in the object.

4 Claims, 10 Drawing Figures

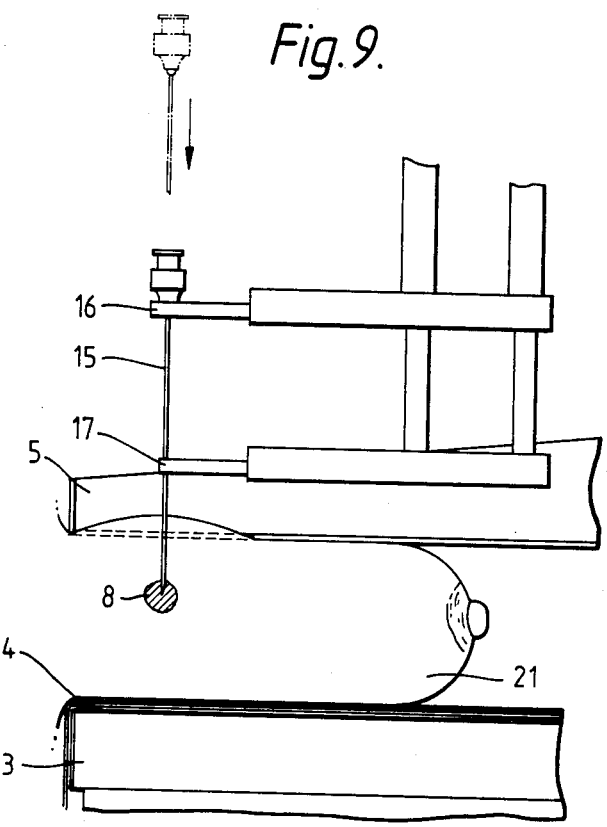
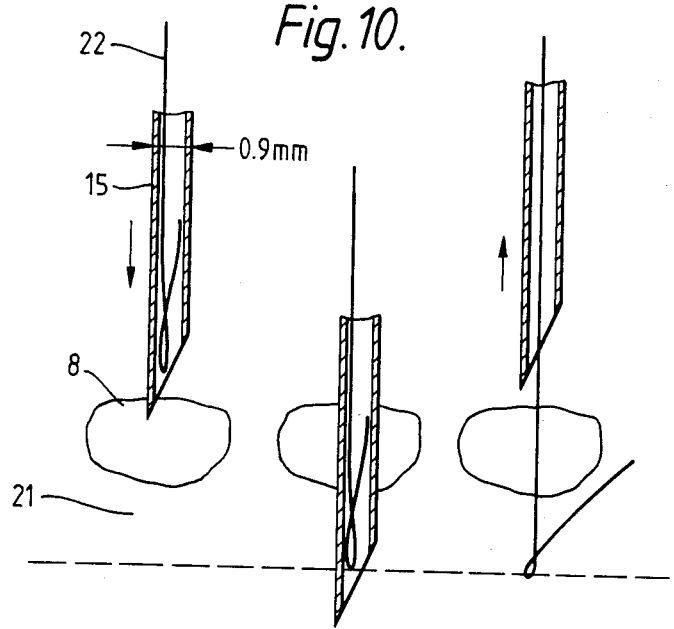

METHOD OF LOCALIZATION

TECHNICAL FIELD

The present invention relates to a method, in conjunction with the X-ray exposure of an object, of localising the three-dimensional position of a spot in the object.

BACKGROUND ART

In many contexts, it is desirable to be able to localise a spot within an object and, for example, to guide and insert an instrument to exact position in the spot. This is of particular importance in breast cancer diagnosis using int. al. fine-needle biopsy which may be considered as included in the clinical and cytological components in triple diagnostics. This triple diagnostics procedure generally includes mammography, clinical examination and cytology. Fine-needle biopsy or fine needle puncture with cytological examination of cell samples from a suspected region provide very reliable positive responses. Furthermore, it is desirable, using fine-needle biopsy, to be able to indicate a spot by means of a thin wire marker for facilitating subsequent surgical excision biopsy.

OBJECT OF THE PRESENT INVENTION

The task forming the basis of the present invention is to realise a method of localising, as simply, reliably and rapidly as possible, the three-dimensional position of a spot in an object, for example a female breast.

SOLUTION

This task is solved according to the present invention in that, after fixation of the object in a pre-determined position, the object is exposed by means of an exposure device in two directions, each on either side of a centre line at right angles to the plane of the image for obtaining a first image print and a second image print, the invention being characterised in that the two-dimensional position of the target spot on the two prints is established in relation to an index on the prints; and that the coordinates of the spot in relation to the indices are processed to obtain control signals for setting of a guidance instrument with means for placing in the target spot in the object. The exposure device and the guidance instrument are placed in the same centre reference from which the right-angle centre line departs. The index is exposed on the print preferably simultaneously with the object for obtaining an exact measurement reference.

ADVANTAGES

The method according to the present invention makes possible the localisation of an optional spot in an object, for example a female breast, with a very high degree of precision in an extremely simple and reliable manner. By applying the method according to the present invention in conjunction with breast cancer diagnosis, it is possible to attain an optimal spot in a female breast for fine-needle puncture, indication or some form of directed therapy in a simple and rapid manner so that the patient need not be subjected to undue stress or excessive discomfort.

BRIEF DESCRIPTION OF THE ACCOMPANYING DRAWINGS

The nature of the present invention and its aspects will be more readily understood from the following brief description of the accompanying Drawings, and discussion relating thereto.

In the accompanying Drawings:

FIG. 9 is, on a larger scale, a side elevation of a number of the parts illustrated in FIGS. 6–8; and FIG. 10 shows, on a larger scale, a region from FIG. 9.

DESCRIPTION OF PREFERRED EMBODIMENT

Figure 1:
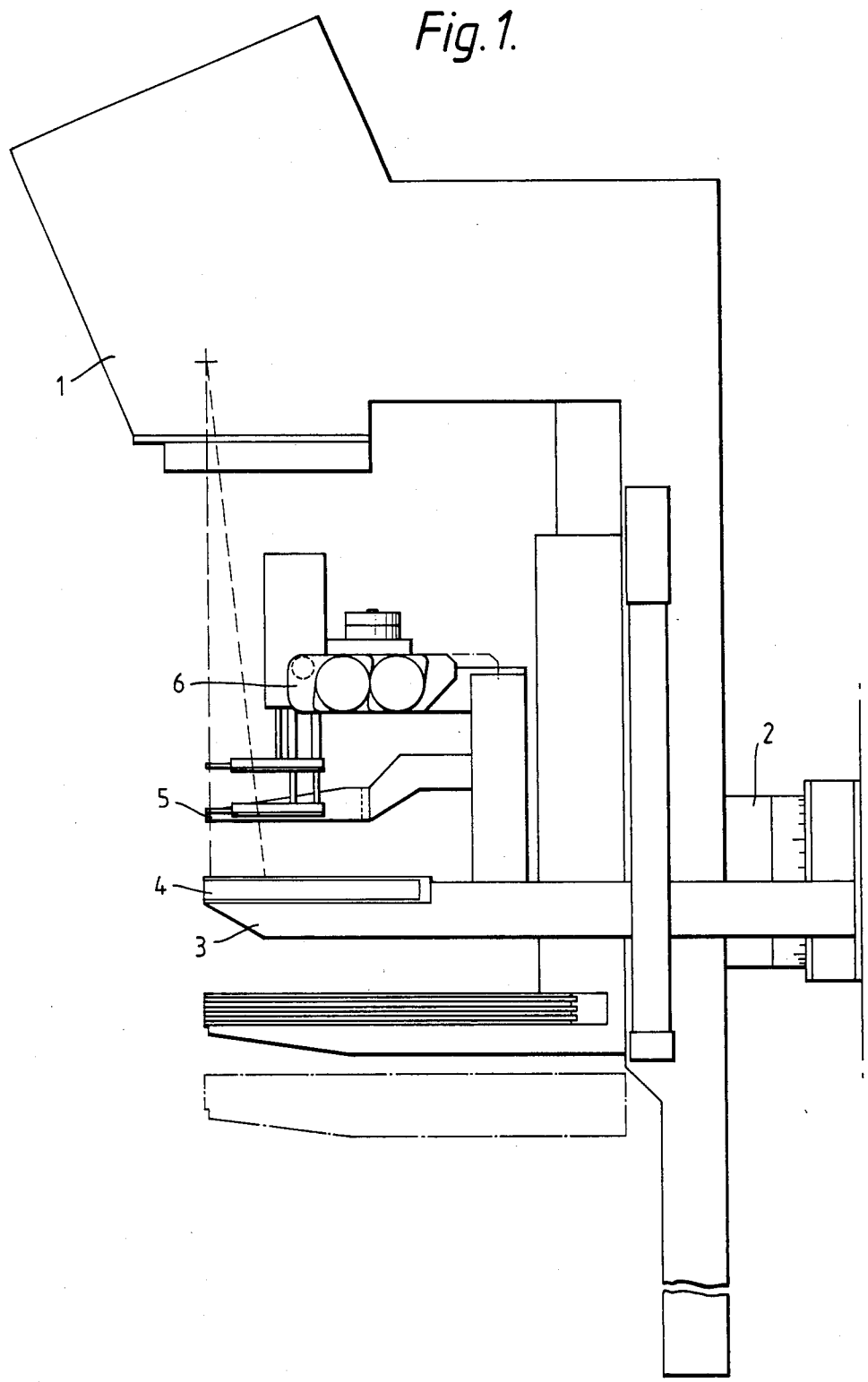
FIG. 1 is a side elevation of a section of an apparatus for carrying out the method according to the present invention.
Figure 6:
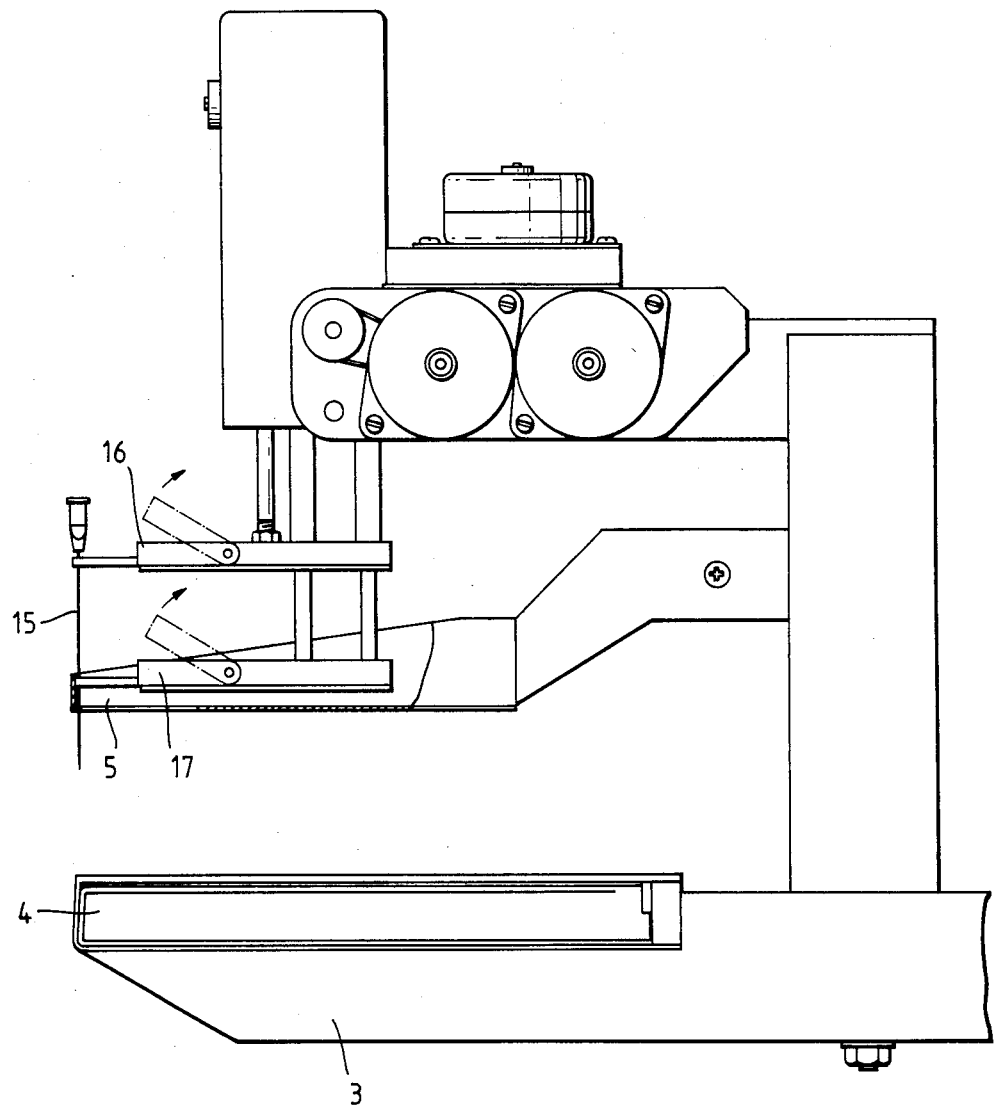
FIG. 6 is a side elevation of parts of an apparatus for carrying out the method according to the present invention.

The method according to the present invention will now be described in greater detail in conjunction with the apparatus for its execution as shown on the Drawings. The apparatus includes int. al. a per se known mammograph 1 which may be of the type designated "Scenograph 500 T". The mammograph 1 is pivotal about a shaft 2 which is provided with a scale for the exact setting of the mammograph 1. A film cassette holder for a film cassette 4 is mounted on an arm 3. A compression plate 5 is disposed above the arm 3 with the film cassette 4. The compression plate 5 is, naturally, vertically movable and has an orifice of, for example, 50×40 mm to make possible the insertion of, for instance, a biopsy needle into a breast which is held in a compressed state by means of the compression plate 5 on the arm, and the film cassette holder 4. The path of radiation from the tube in the mammograph 1 generating the X-rays is illustrated by ghosted lines, the radiation path impinging upon a film in the film cassette holder 4 for generating an exposed print which depicts the exposed breast region. The apparatus illustrated in FIG. 1 further includes a guidance instrument 6 which is shown in greater detail in FIGS. 6, 7 and 8 and parts thereof in FIG. 9. The above-mentioned parts 3, 4 and 5 may be considered as forming part of the guidance instrument 6, since the parts 3, 4 and 5 are fixed in relation to the mammograph 1, pivotal about the shaft 2. The compression plate 5 is transparent to X-rays so that a greater portion of the object is exposed than the surface located directly beneath the orifice in the compression plate 5.

Figure 2:
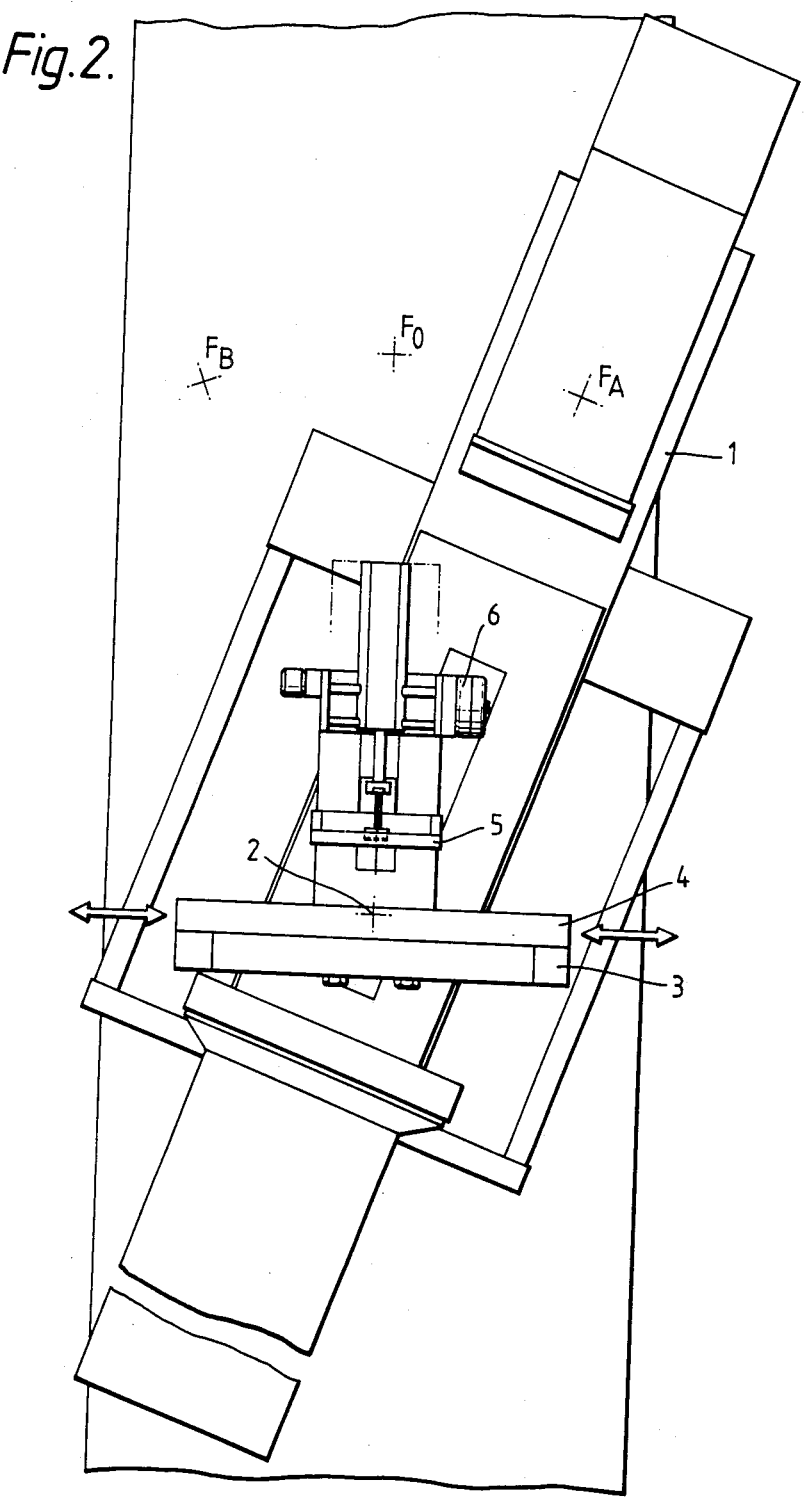
FIG. 2 is a front elevation of the apparatus of FIG. 1.

FIG. 2 illustrates in greater detail the pivotal capacity of the mammograph 1 about the shaft 2. For executing the method according to the present invention, a first exposure is taken with the mammograph 1 in the position shown in FIG. 2 from the focal point FA with the film cassette in a first position for generating a film print A, whereafter the mammograph is pivoted and the film cassette is shifted for exposure in the focal point FB and for generating a film print B.

Figure 3:
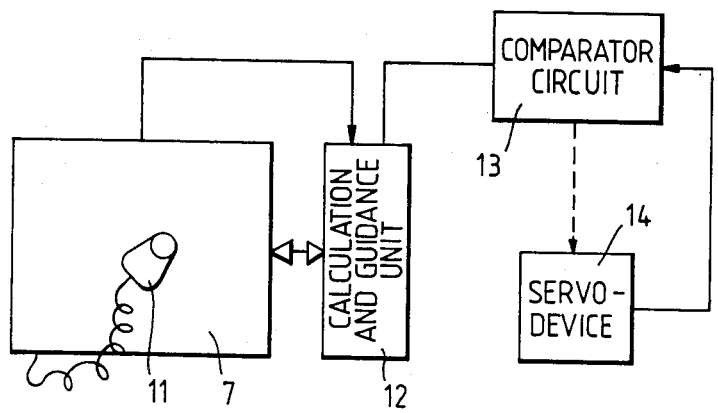
FIG. 3 is a block diagram of parts included in an apparatus for carrying out the method according to the present invention.
Figure 4:
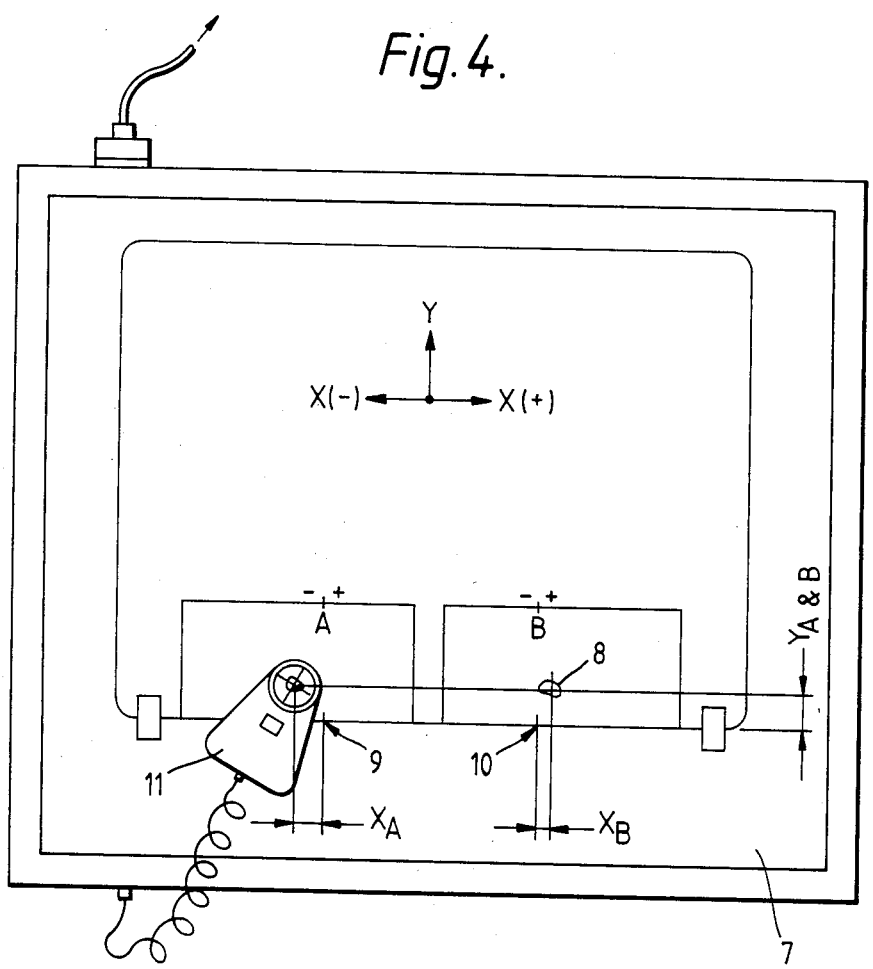
FIG. 4 is a top plan view of the parts illustrated in FIG. 3 but shown in greater detail.
Figure 5:
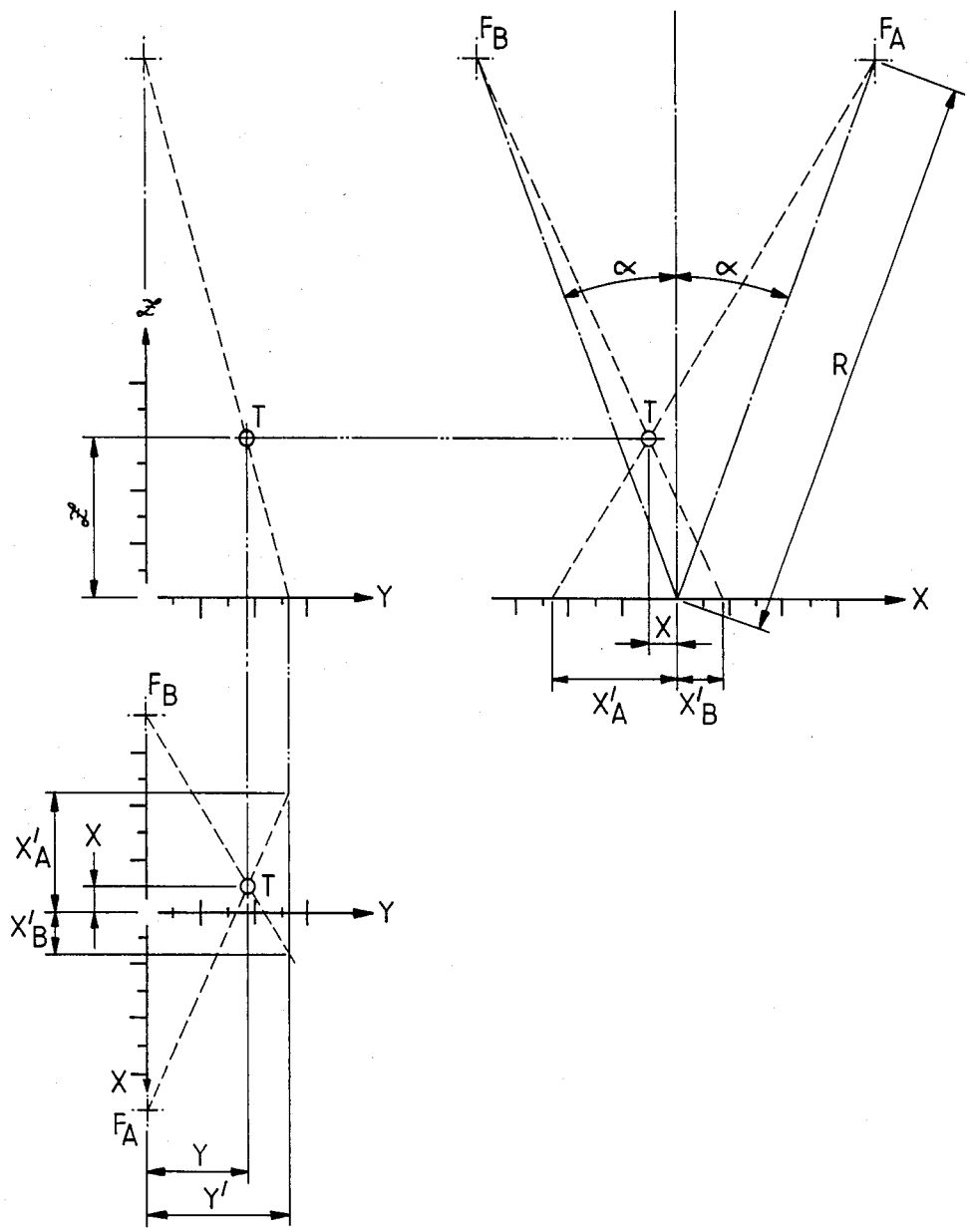
FIG. 5 illustrates the geometric conditions for the present invention.

Furthermore, for carrying out the method according to the present invention, use is made of the parts illustrated in block form in FIGS. 3 and 4, while employing the graphic principle illustrated in FIG. 5. The exposed prints A and B are placed on a measurement pad 7. The prints show, apart from the spot 8 which it is desirable to localise and examine more closely, also an index mark 9 on print A and an index mark 10 on print B. The film cassette is arranged such that the index 9 and a letter A or other marking are exposed simultanesouly with the object on the print A, and the index 10 together with the letter B on print B, so as to avoid confusion and to realise an exact reference on each print.

A monitoring unit 11 is included in the measurement pad 7 and is generally entitled a cursor. For carrying out the measurement, the cursor is first placed on the index of each respective print and thereafter, directly above the spot which it is desired to localise, so as to obtain the polar coordinates of the spot. The measurement pad 7 is coupled to a calculation and guidance unit 12 in which the geometric calculations illustrated in FIG. 5 are carried out and in which signals are generated for operating servo-devices 14 in the guidance instrument 6 proper, by the intermediary of a comparator circuit 13 with figure display in those cases when it is desirable to carry out automatic setting of the guidance instrument 6 and; in such an event, re-hook-up to the servo-devices is effected from the guidance instrument 6.

The servo-devices 14 may be replaced by manual means and some form of indicator for converting the signals from the calculation unit 12 to setting values. This is carried out in the comparator circuit 13 which may also be considered as a difference and trend indicator which includes a figure display, by means of which the guidance instrument is set, and a possible fine-needle can be placed in the target spot.

Figure 7:
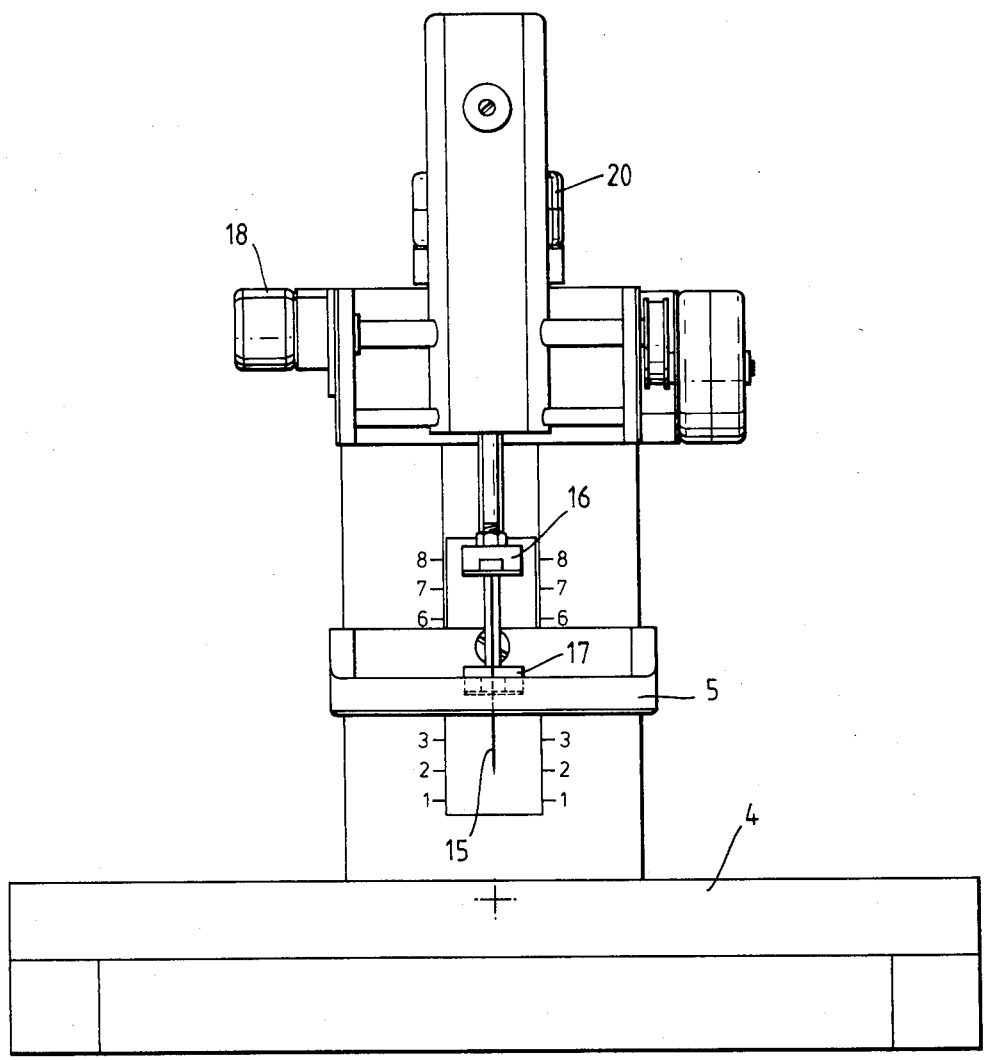
FIG. 7 is a front elevation of the parts illustrated in FIG. 6.
Figure 8:
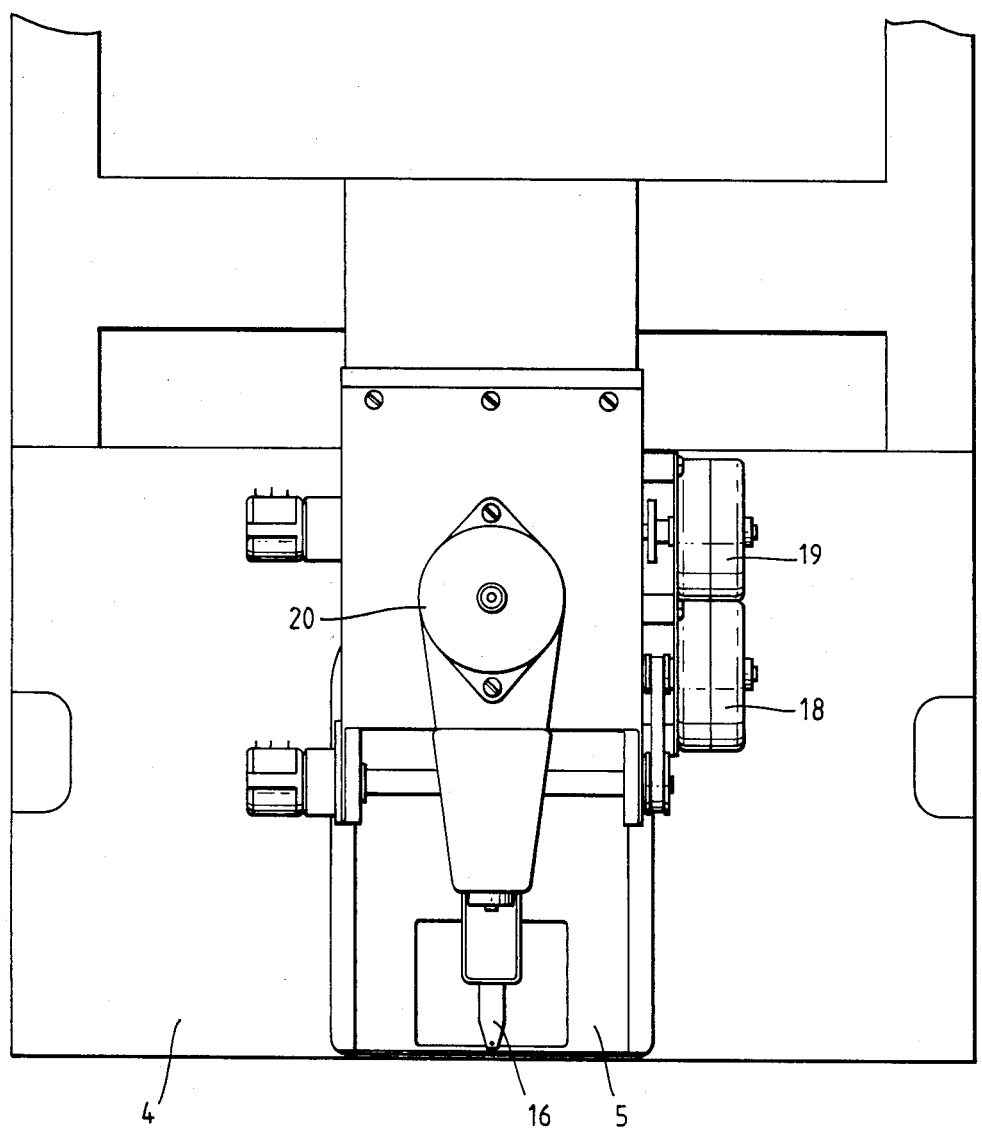
FIG. 8 is a top plan view of the parts shown in FIGS. 6 and 7.

FIGS. 7, 8 and 9 show the guidance instrument 6 in greater detail and, as will be apparent from these Figures, the arm 3, the film cassette holder 4 and the compression plate 5 are associated parts of the guidance instrument. In the orifice in the compression plate 5, it is possible to move an upper needle retainer 16 and a lower needle retainer 17 on the X, Y, and Z axes. The lower needle retainer 17 is vertically movable independently of the upper needle retainer 16. The needle retainers 16 and 17 are guided using servo motors 18, 19 and 20, and the desired position of the needle tip can be read-off on displays for the exact localisation of the needle tip in relation to the value calculated using the calculation unit 12 in such a manner that the needle tip can be placed in the spot or region 8 illustrated in FIG. 9.

Adjustment of the guidance instrument 6, and, thereby, the needle retainers is suitably effected such that the position of the needle retainers 16, 17 on the X, Y and Z axes is first set, whereafter the fine-needle is placed in the retainers 16 and 17, and, on abutment against the upper retainer 16, the needle tip is in the correct position. This adjustment may very well be executed using the servo devices, while the vertical motion of the lower needle retainer 17 or needle guider is effected manually. With the needle retainers 16 and 17 in the correct position, an acoustic signal is generated which may possibly also be combined with a light signal. This is illustrated in greater detail in FIG. 9. In this case, it is desirable to carry out closer examination of region 8 of the female breast 21, which is compressed between the film cassette holder 4 and the compression plate 5 and has been in such state during exposure of the two prints A and B and a subsequent input using the cursor on the measurement pad 7 and the following calculations of adjustments values for the guidance instrument 6. It should, here, be observed that all parts included in the apparatus are, as it were, "on-line", which ensures a very rapid execution of the method.

According to FIG. 9, the needle 15 shall be moved from the position shown by ghosted lines to the position shown by solid lines. After setting of the X and Y axes of the needle retainers 16 and 17, the lower needle retainer is employed for insertion of the biopsy needle to the region 8. Different steps may be implemented, depending on the structure of the biopsy needle.

FIG. 10 illustrates how a marker wire 22 is placed in the region 8 so as, on later surgical excision, to guide the surgeon to the region 8. It is an extremely delicate, if not entirely impossible operating to find region 8 without the help of the wire marker, since the region 8 may be as small as one or two mm.

The method according to the present invention greatly facilitates breast cancer diagnosis and, above all, makes for developments of the earlier mammography in an extremely rational and reliable manner. The method according to the present invention also makes for an extensive development of the methodology of mammography examination without entailing greatly increased burdening of therapeutic activities. The present invention also provides the possibility of a considerable refinement of therapeutic methods in an extremely gentle and careful manner and at low cost. Employment of the method according to the present invention also makes for considerably earlier identification of malignant areas during the most occult stages, whereby treatment without surgery may be conceivable.

I claim:

1. A method for localizing the three-dimensional position of a spot in an object in conjunction with the x-ray exposure of said object comprising clamping the object in a predetermined position, obtaining a first print of at least said spot in said object by exposure of the object to a source of x-rays in a first direction from a first position on one side of a center line at right angles to the image plane of the first print, providing a first index on said first print, and with the object remaining clamped in the same predetermined position, obtaining a second print of said spot by exposure of the object to said source of x-rays in a second direction from a second position on the other side of said center line, providing a second index on the second print, establishing the two-dimensional position of the spot on the two image prints in relation to the index on the prints, and processing the coordinates of the spot in relation to the indices for determination of the three dimensional position of said spot so as to enable control of a guidance instrument to the spot located in the object.

2. The method as recited in claim 1, wherein the prints are exposed together with their indexes on one and the same film for placement on a measurement table after development.

3. The method as recited in claim 1, wherein the first print and the second print are exposed on film in a cassette, which is shifted from one position for exposure of the first print to another position for exposure of the second print, and an index is exposed on the prints at the same time as the object.

4. The method as recited in claim 1, wherein the source of x-rays and guidance instrument are placed in the same center line.

* * * * *